United States Patent [19]

Jarvis, Jr. et al.

[11] Patent Number: 4,495,288

[45] Date of Patent: * Jan. 22, 1985

[54] METHOD OF CULTURING ANCHORAGE DEPENDENT CELLS

[75] Inventors: Allan P. Jarvis, Jr., Newburyport, Mass.; Franklin Lim, Richmond, Va.

[73] Assignee: Damon Biotech, Inc., Needham Heights, Mass.

[*] Notice: The portion of the term of this patent subsequent to Oct. 5, 1999 has been disclaimed.

[21] Appl. No.: 484,627

[22] Filed: Apr. 13, 1983

Related U.S. Application Data

[63] Continuation of Ser. No. 243,586, Mar. 13, 1981, abandoned, which is a continuation-in-part of Ser. No. 24,600, Mar. 28, 1979, Pat. No. 4,352,883, which is a continuation-in-part of Ser. No. 935,413, Oct. 28, 1978, abandoned.

[51] Int. Cl.$^3$ .......................... C12N 5/00; C12N 5/02; C12N 11/00; C12N 11/04
[52] U.S. Cl. .................................... 435/241; 435/174; 435/182; 435/240
[58] Field of Search ................ 435/174, 182, 240, 241

[56] References Cited

U.S. PATENT DOCUMENTS

| 3,730,841 | 5/1973 | Forgione et al. | 435/182 |
| 4,189,534 | 2/1980 | Levine et al. | 435/241 X |
| 4,266,032 | 5/1981 | Miller et al. | 435/241 |
| 4,352,883 | 10/1982 | Lim | 435/240 X |

FOREIGN PATENT DOCUMENTS

| 2046209 | 11/1980 | United Kingdom | 435/182 |
| 2083827 | 3/1982 | United Kingdom . | |

*Primary Examiner*—David M. Naff
*Attorney, Agent, or Firm*—Lahive & Cockfield

[57] ABSTRACT

Disclosed is a method of growing anchorage-dependent cells: cells of the type which normally undergo mitosis only when anchored on a substrate, e.g., fibroblasts or epithelial cells. The method comprises the steps of encapsulating a seed culture of the cells within a semipermeable membrane and suspending the capsules in a growth medium. The interior surfaces of the capsule membrane and/or collagen enclosed within the capsules serve as a substrate for the cells. The ratio of the available substrate surface area to the volume of the culture may be large, thereby allowing the cells to be grown substantially throughout the volume of the culture medium.

10 Claims, 1 Drawing Figure

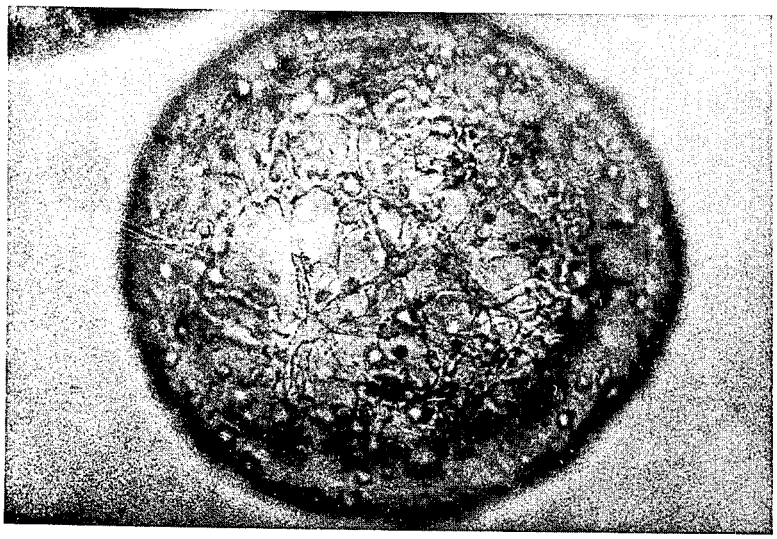

METHOD OF CULTURING ANCHORAGE DEPENDENT CELLS

REFERENCE TO RELATED APPLICATIONS

This application is a continuation of copending U.S. application Ser. No. 243,586, filed Mar. 13, 1981, and now abandoned, which was a continuation-in-part of copending application Ser. No. 24,600, filed Mar. 28, 1979, now U.S. Pat. No. 4,352,883, which was a continuation-in-part of U.S. application Ser. No. 935,413, filed Oct. 28, 1978, now abandoned. Related U.S. application Ser. Nos. 243,584 and 243,583, both now abandoned were filed on even date herewith. The disclosures of all of the foregoing applications are incorporated herein by reference.

BACKGROUND OF THE INVENTION

This invention relates to a method of culturing anchorage dependent cells, that is, cells of the type which normally must be grown as one or more layers on a substrate and cannot be grown in suspension.

Advances in cellular biology have shown that the anchorage dependent cells of various higher organisms can produce small quantities of substances having significant potential or demonstrable utility for the treatment of disease, e.g., interfereon. Such cells are also useful for research purposes.

In such cell cultures there is an ever present danger of bacterial or other contamination. Also, in most instances the quantities of the substance of interest produced by the cell cultures are very small. Since, unlike suspension cultures, anchorage dependent cells cannot be cultured to fill a volume, there is believed to be no presently existing practical method of growing the large numbers of cells required for production of significant quantities of substances of interest produced by such cells.

Currently, anchorage dependent cells such as normal fibroblasts and certain kidney and epithelial cells must be cultured on a substrate. Plastic sheets for use as substrates are commercially available. Some types of anchorage dependent cells with reproduce until the sheet is covered with a monolayer of cells and then cease multiplying. Others will continue to multiply to form one or more additional layers above the first.

SUMMARY OF THE INVENTION

This invention provides a method of culturing anchorage dependent cells in suspension and thereby enables greater numbers of cells to be grown per unit volume of culture medium as compared with monolayer cultures.

In accordance with the invention, a seed culture of anchorage dependent cells is encapsulated within a plurality of microcapsules comprising semipermeable membranes. Synthesis of the membranes is controlled so that they have a selected upper limit of permeability, that is, the membranes define micropores of dimensions sufficient to allow passage of molecules having a molecular weight up to, for example, $2 \times 10^5$ daltons, but substantially preclude passage of materials of higher molecular weight. The capsule membrane thus defines a microenvironment within which the cells together with high molecular weight serum components are confined, but which allow the cells free access to lower molecular weight cell nutrients such as amino acids, and allow low molecular weight cell metabolites to exit the environment.

The microcapsules containing cells are then dispersed in a conventional culture medium. The interior surfaces of the capsule membrane and/or certain high molecular weight water-dispersible materials which are included in the microcapsule act as a substrate to which the cells attach. Because the ratio of the surface area of the capsules to the volume of the extracapsular medium may be quite large, individual cells are afforded adequate access to required nutrients, and the area on which the cells can grow is increased as compared with conventional monolayer cultures. Generally, the average diameter of the microcapsules may be varied between a few microns to a millimeter or more. A preferred average size is on the order of 100–500 micrometers in diameter.

If an anchorage substrate such as collagen or the like is included within the capsules, then fibroblasts also grow inwardly of the capsule membranes and will display normal fibroblastic morphology.

It is an object of the invention to provide an improved method of culturing anchorage dependent cells. Another object is to improve the yield of anchorage dependent or contact inhibited cells grown in vitro. Another object is to provide throughout the volume of a cell growth medium a large surface area suitable as a substrate for anchorage dependent cells. Another object is to provide a method of growing cells which can produce interfereon. These and other objects and features of the invention will be apparent from the description which follows and from the drawing wherein the sole figure is a photomicrograph (200×) showing anchorage dependent cells grown within a microcapsule in accordance with the invention and illustrating classical fibroblastic morphology.

DESCRIPTION

The broad concept of the invention is to provide a multiplicity of semipermeable membranes about individual cells or groups of cells to act as a high surface area substrate to which the cells can anchor and/or to confine a high molecular weight material within microcapsules to serve as an anchorage substrate. Cells which grow in suspension may also be encapsulated as taught herein and in the above-referenced copending applications. The microcapsules serve as a microenvironment for the cells together with at least high molecular weight components of its culture medium, and separate the cells from an extracapsular aqueous medium. Bacteria and other relatively large contaminants cannot penetrate the membranes.

Anchorage dependent cells of mammalian origin, such as fibroblast, epithelial, or kidney cells require for ongoing viability the presence of serum components, a portion of which may have a molecular weight in excess of the upper permeability limit of the membranes. Such components may be included with the encapsulated cells and need not be present in the extracapsular medium.

It is required also to include within the microcapsules a high molecular weight material to serve as an anchoring substrate. Collagen, a natural protein which is a major constituent of connective tissues, has been used with success for this purpose. Other compatible high molecular weight, water dispersible proteins may also be used, e.g., polylysine. If the proteins have free amino groups, they may be rendered water-insoluble by reaction with a water-soluble gum during membrane formation as disclosed hereinafter. The use of such materials is believed to result in the creation of a matrix within the intracapsular volume. The inclusion of such a material can improve the cell density within the capsules as the cells grow within the intracapsular volume instead of or in addition to the growth about the interior of the capsule membrane.

The encapsulated seed culture is then suspended in a suitable growth medium of the type employed for growth of conventional cultures. Serum proteins which are not injested by the cells may be omitted from the extracapsular medium. However, pH, temperature, ionic concentration, and the like should be the same as in conventional media. Also, oxygen and $CO_2$ transfer may be promoted by the same means as in conventional cultures, as these dissolved gasses freely traverse the membrane.

Incubation of the encapsulated cell culture results in cell mitosis. Fibroblast cell growths display classical fibroblastic morphology and form arrays of cells on the interior of the membrane or on the anchoring substrate contained within the capsules. Fresh growth medium may be supplied as required either on a continuous or intermittent basis by change of the extracapsular medium. If the purpose of the culture is to produce a cell metabolite of interest, the metabolite may be harvested either from the intracapsular volume or the extracapsular medium, depending on its molecular weight and the upper permeability limit of the membranes (see copending application Ser. No. 243,583, now abandoned). In a preferred embodiment of the process, the membranes are of a type which may be selectively disrupted without damage to the cells. This allows the cells to be released from the capsules as desired (see co-pending application Ser. No. 243,584, now abandoned).

One reason for releasing the cells after their growth period is to stimulate the production of a substance of interest by the cells. An example is the production of interferon from human fibroblasts, leukocytes, or lymphoblastoid cells which are induced to excrete interferon by treatment with certain viruses or high molecular weight nucleic acids. In such a situation, if the upper permeability limit of the membranes is less than the molecular weight of the inducing factor, the cells must be subjected to interferon induction prior to encapsulation, or the capsule membranes, after culture of the cells, must be selectively disrupted to allow such high molecular weight materials to come into contact with the cell.

The process of the invention depends on one's ability to form semipermeable membranes about cells without simultaneously adversely affecting their ongoing viability. One suitable encapsulation process is set forth in detail below.

CELL ENCAPSULATION

The tissue or cells to be encapsulated are suspended in an aqueous medium preferably suitable for growth of the cell type involved. Media suitable for this purpose are available commercially. The average diameter of the material to be encapsulated can vary widely between a few micrometers to about a millimeter. However, best results are achieved with capsules of a size in the range of 100–500 micrometers. Individual anchorage dependent cells such as fibroblasts from human or other animal tissues, kidney cells, and epithelial cells may be encapsulated as desired. Also other cells such as leukocytes, lymphoblastoids, pancreatic beta cells, alpha cells, delta cells, various ratios thereof, or other tissue units may be encapsulated.

The ongoing viability of such living matter is dependent, inter alia, on the availability of required nutrients, oxygen transfer, absence of toxic substances in the medium, and the pH of the medium. Heretofore, it has not been possible to maintain such living matter in a physiologically compatible environment while simultaneously encapsulating. The problem has been that the conditions required for membrane formation have been lethal or harmful to the tissue, and prior to the invention of the above-referenced application Ser. Nos. 953,413 and 24,600, no method of membrane formation which allowed tissue to survive in a healthy state had been forthcoming.

However, it has been discovered that certain water-soluble substances which are physiologically compatible with living tissue and can be rendered water-insoluble to form a shape-retaining, coherent mass, can be used to form a "temporary capsule" or protective barrier layer about individual cells or groups of cells and that this temporary capsule can be treated to deposit a more permanent semipermeable membrane about the cells without damage to the cells. Such a substance is added, typically at a concentration on the order of less than 1.0 weight percent, to the tissue culture medium which also contains cells of the seed culture, serum components (if required), and collagen or another high molecular weight, water-dispersible material which acts as an anchoring substrate. The concentration of the material employed as a substrate should be within the range of about 10 ug/ml to about 1 but is preferably on the order of 100–500 ug/ml.

The solution is then formed into droplets containing tissue together with its medium and is immediately rendered water-insoluble and gelled, at least in a surface layer. Thereafter, the shape-retaining temporary capsules are provided with a more permanent membrane which may itself subsequently be selectively disrupted if it is desired to release the tissue without damage. Where the material used to form the temporary capsules permits, the capsule interior may be reliquified after formation of the permanent membrane. This is done by reestablishing the conditions in the medium at which the material is soluble.

The material used to form the temporary capsules may be any non-toxic, water-soluble material which, by a change in ionic environment or concentration, can be converted to a shape-retaining mass. The material should also contain plural, easily ionized anionic moieties, e.g., carboxyl groups, which can react by salt formation with polymers containing plural cationic groups. As will be explained below, use of this type of material enables one to deposit a permanent membrane of a selected upper limit of permeability (generally no greater than 100,000 to 150,000 daltons) without difficulty in surface layers of the temporary capsule.

The presently preferred materials for forming the temporary capsule are acidic, water-soluble, natural or synthetic polysaccharide gums. Such materials are commercially available. They are typically extracted from vegetable matter and are often used as additives to various foods. Sodium alginate is the presently preferred water-soluble gum. Alginate in the molecular weight range of 150,000+ daltons may be used, but because of its molecular dimensions and viscosity will usually be unable to permeate the finally formed capsule membranes. Lower molecular weight alginate, e.g., 50,000–80,000 daltons, is more easily removed from the intracapsular volume by diffusion through a membrane of sufficient porosity and is therefore preferred. Other useable gums include acidic fractions of guar gum, carageenan, pectin, tragacanth gum, or xanthan gum.

These materials comprise glycoside-linked saccharide chains. Their free acid groups are often present in the alkali metal ion form, e.g., sodium form. If a multivalent ion such as calcium or strontium is exchanged for the alkali metal ion, the water-soluble polysaccharide molecules are "cross-linked" to form a water-insoluble, shape-retaining gel which can be resolubilized on removal of the ions by ion exchange or via a sequestering agent. While essentially any multivalent ion which can form a salt with the acidic gum is operable, it is preferred that physiologically compatible ions, e.g., calcium, be employed. This tends to preserve the tissue in the living state. Other multivalent cations can be used. Magnesium ions are ineffective in gelling sodium alginate.

A typical solution composition comprises equal volumes of a cell culture in its medium (with an anchoring substrate) and a one or two percent solution of gum in physiological saline. When employing sodium alginate, a 1.0 to 1.5 percent solution has been used with success. Collagen or another high molecular weight water-dispersible protein or polypeptide, either natural or synthetic, may be included in the cell culture, and will be confined within the intracapsular volume of the finally formed capsules. If a polymer having plural cationic groups is employed, e.g., polylysine, the cationic groups react with anionic sites in the water-soluble gum to form a substantially water-insoluble matrix intertwined with the gum. Preferred concentrations for such materials are on the order of 100–500 ug per ml of suspension (including gum solution).

In the next step of the encapsulation process, the gum solution containing the tissue is formed into droplets of a desired size, and the droplets are immediately gelled to form shape-retaining spherical or spheroidal masses. The drop formations may be conducted as follows.

A tube containing an aqueous solution of multivalent cations, e.g., 1.5% $CaCl_2$ solution, is fitted with a stopper which holds a drop forming apparatus. The appratus consists of a housing having an upper air intake nozzle and an elongate hollow body friction fitted into the stopper. A 10 cc syringe equipped with a stepping pump is mounted atop the housing with, e.g., a 0.01 inch I.D. Teflon coated needle passing through the length of the housing. The interior of the housing is designed such that the tip of the needle is subjected to a constant laminar air flow which acts as an air knife. In use, with the syringe full of solution containing the material to be encapsulated, the stepping pump is actuated to incrementally force droplets of solution from the tip of the needle. Each drop is "cut off" by the air stream and falls approximately 2.5 cm into the $CaCl_2$ solution where it is immediately gelled by absorption of calcium ions. The distance between the tip of the needle and the surface of the $CaCl_2$ solution is great enough, in this instance, to allow the sodium alginate/cell suspension to assume the most physically favorable shape; a sphere (maximum volume for minimum surface area). Air within the tube bleeds through an opening in the stopper. This results in "cross-linking" of the gel and in the formation of a high viscosity shape-retaining protective temporary capsule containing the suspended tissue and its medium. The capsules collect in the solution as a separate phase and may be separated by aspiration.

In the next step of the process, a semipermeable membrane is deposited about the surface of the temporary capsules by "cross-linking" surface layers. This may be effected by subjecting the gelled temporary capsules to an aqueous solution of a polymer containing cationic groups reactive with anionic functionalities in the gel molecules. Polymers containing acid reactive groups such as free imine or amine groups are preferred. In this situation, the polysaccharide gum is crosslinked by interaction (salt bond formation) between the carboxyl groups and the amine or imine groups. Permeability can be controlled within limits by selecting the molecular weight of the cross-linking polymer used and by regulating the concentration of the polymer solution and the duration and temperature of exposure. A solution of polymer having a low molecular weight, in a given time period, will penetrate further into the temporary capsules than will a high molecular weight polymer. The degree of penetration of the cross-linker has been correlated with the resulting permeability. In general, the higher the molecular weight and the less penetration, the larger the pore size. Broadly, polymers within the molecular weight range of 3,000 to 100,000 daltons or greater may be used, depending on the duration of the reaction, the concentration of the polymer solution, and the degree of permeability desired. One successful set of reaction conditions, using polylysine of average molecular weight of about 35,000 daltons, involved reaction for two minutes, with stirring, of a physiological saline solution containing 0.0167 percent polylysine. This results in membranes having an upper permeability limit of about 100,000 daltons. Optimal reaction conditions suitable for controlling permeability in a given system can readily be determined empirically in view of the foregoing guidelines. Using this method it is possible to set the upper permeability limit of the membranes at a selected level generally below about 150,000 daltons.

Examples of suitable cross-linking polymers include proteins and polypeptides, either natural or synthetic, having free amino or imino groups, polyethyleneamines, polyethyleneimines, and polyvinylamines. Polylysine, in both the D and L forms, has been used with success. Proteins such as polyarginine, polycitrulline, or polyornithine are also operable. Polymers in the higher range of positive charge density, e.g., polyvinylamine, vigorously adhere to the anionic groups of the gel molecules to form stable membranes, but the membranes are somewhat difficult to disrupt.

Treatment with a dilute solution of gum or a switterionic buffer will tie up free amino groups on the surfaces of the capsules which otherwise may impart to the capsules a tendency to clump.

At this point in the encapsulation, capsules may be collected which comprise a semipermeable membrane surrounding a gelled solution of gum, cell-type compatible culture medium, cells, and an internal matrix of collagen or another anchorage substrate. Since mass transfer should be promoted within the capsules and across the membranes, it is preferred to reliquify the gel to its water-soluble form. This may be done by re-establishing the conditions under which the gum is a liquid, e.g., removing the calcium or other multifunctional cations from the interior gel. The medium in the capsule can be resolubilized simply by immersing the capsules in phosphate buffered saline, which contains alkali metal ions and hydrogen ions. Monovalent ions exchange with the calcium or other multifunctional ions within the gum when the capsules are immersed in the solution with stirring. Sodium citrate solutions may be used for the same purpose, and serve to sequester the divalent ions.

Cell cultures encapsulated as described above may be suspended in growth medium designed specifically to satisfy all of the requirements of the particular cell type involved and will continue to undergo normal in vitro metabolism and mitosis. If the culture requires an environment of high molecular weight components such as serum components, these may be omitted from the extracapsular medium. Typically, the components normally ingested by cells are of relatively low molecular weight and readily diffuse across the capsule membranes into the microenvironment of the cells where they permeate the cell membrane. Metabolites of the cells which are excreted into the intracapsular medium, if they have a molecular weight below the upper limit of permeability of the capsule membrane, likewise diffuse thereacross and collect in the extracapsular medium.

The encapsulated cells are grown under conditions of, e.g., temperature, pH, and ionic environment, identical to conventional cultures. Cell metabolites may be harvested from the extracapsular medium or from the intracapsular volume by conventional techniques. However, the culturing technique disclosed herein has the following advantages:

1. The cells of the culture are protected from contamination by factors having dimensions in excess of the upper permeability limit of the membranes. This means that sterility requirements normally incident to culturing procedures can be somewhat relaxed, since microorganisms cannot reach the encapsulated cells.

2. The capsules in effect immobilize the cells within an environment in which enclosed high molecular weight materials are confined, yet lower molecular weight cell nutrients and products are readily removed and introduced. This allows the nutrient medium to be intermittently or continuously collected and supplemented as desired, without disturbing the cells.

3. Substances of interest produced by the cells are more easily recovered. Cell products of molecular dimensions small enough to permeate the capsule membranes collect in the extracapsular medium in admixture with nutrients. However, high molecular weight serum components and the like are not released into the extracapsular medium, thus simplifying recovery of a cell product of interest. Cell products of molecular dimensions in excess of the upper permeability limit of the membranes collect within the capsules. These may be recovered in relatively concentrated form by isolating the capsules and subsequently selectively disrupting the membranes using, for example, the technique disclosed hereinafter.

4. The intracapsular volume provides an environment well suited for cell division. Suspension cultures have been observed to undergo mitosis within the capsule. Anchorage dependent cells which in normal cultures grow in a two-dimensional monolayer multiply to form an array within the capsule. Such cells use the interior surfaces of the membrane as a substrate and/or anchor to the high molecular weight materials set forth above which are disposed within the capsule. This leads to significant increases in cell density as compared with conventional cultures. The ongoing viability of such cell clusters is aided by the fact that the surface area to volume ratios of the capsules can be quite large, and thus all cells have access to required nutrients, oxygen, etc.

In certain situations it is advantageous to selectively disrupt the capsule membranes to release the cells without damage. One notable example is in the production of interferon (IFN). Cells capable of producing IFN must be subjected to certain viruses or nucleic acids in preparation for the IFN production stage. Also, in several IFN induction procedures, reagents are added to the culture to inhibit protein synthesis. Accordingly, the growth stage of the culturing process must be conducted under conditions quite different from the IFN induction stage. If the substances used for IFN induction are of a molecular weight in excess of the upper permeability limit of the capsule membranes (as will be the case in virus inductions) the induction process cannot be accomplished in the encapsulated cell culture. Accordingly, IFN producing cells, if grown within the capsule, would have to be released by disruption of the membrane in order to be subjected to the induction process.

DISRUPTION OF MEMBRANES

Cells confined in membranes of the type set forth above may be released by a process involving commercially available reagents having properties which do not significantly adversely affect the encapsulated cells. First, the capsules are separated from their suspending medium, washed thoroughly to remove any contaminants present on the exterior of the microcapsules, and then dispersed, with agitation, in a mixed solution of monatomic, multivalent cations such as calcium ions and a polymer having plural anionic moieties such as a salt of a polysulfonic or polyphosphoric acid. Heparin, a natural sulfonated polysaccharide, is preferred for this step. The anionic charge density of the polymer used should be equal to or preferably greater than the charge density of the acidic gum originally employed to form the membranes. The molecular weight of the polymer should be at least comparable to and preferably greater than the molecular weight of the polymer having plural cationic groups used in forming the membrane. Within the suspension of capsules in the mixed solution, the calcium ions compete with the cationic polymer chains used to form the membrane for anionic sites on the water-soluble gum. Simultaneously, the heparin or other polymer having plural anionic moieties dissolved in the solution competes with the anionic gum in the membrane for cationic sites on the polymer chains. This results in a water-dispersable or preferably water-soluble complex of e.g., polylysine and heparin, and in association of the monatomic cations with molecules of the gel.

This step renders the membrane suseptible to dissolution upon subsequent exposure to a sequestering agent which completes the disruption process by taking up monatomic ions from the gel. Capsule membrane debris which remains in the medium, if any, can be easily separated from the cells.

The currently preferred solution for the first stage of the selective disruption process comprises 1.1% calcium chloride (w/v) and between 500 to 1,500 units of heparin per milliliter of solution. A volume of microcapsules is added to this solution sufficient to constitute between about 20% and 30% of the total volume of suspension. Calcium chloride and heparin are preferred since both reagents are physiologically compatible with most cells and therefore minimize the possibility of cell damage. Mixtures of strontium salts or other multivalent cations (but not Mg++ ions) may also be used together with the polysulfonic or polyphosphoric acid salts of the type set forth above.

In general, the concentrations of monatomic ions and anionic polymer used in this step may vary widely. Optimum concentrations may be readily determined empirically, and depend on exposure time as well as the particular polymer used to form the membranes.

The currently preferred sequestering agent for performing the selective disruption is sodium citrate, although other alkali metal citrate salts and alkali metal EDTA salts may also be used. When sodium citrate is employed, the optimum concentration is on the order of 50-60 mM. It is preferred to dissolve the citrate or other sequestering agent in isotonic saline so as to minimize cell damage.

The invention will be further understood from the following non-limiting examples.

EXAMPLE 1

Humsn Fibroblasts

Human fibroblasts obtained by treating conventional monolayer culture with trypsin and EDTA for 5 minutes at 37° C. in a known manner are suspended in a complete growth medium (CMLR 1969, Connaught Laboratories) supplemented with 40% (v/v) purified fetal calf serum, 0.8% sodium alginate (Sigma) and 200 ug/ml purified calf skin collagen. The density of the cell suspension is about $1.5 \times 10^7$ cells/ml.

Next, a 1.5 percent calcium chloride solution is used to gel droplets formed by using a drop forming apparatus as described above. Droplets on the order of 50-500 microns in diameter leave the tip of the needle and immediately gel upon entering the calcium solution.

After 5 minutes, the supernatant solution is removed by aspiration. The gelled capsules are then transferred to a beaker containing 15 ml of a solution comprising one part of a 2% 2 (cyclohexylamino) ethane sulfonic acid buffer solution in 0.6% NaCl (isotonic, ph=8.2) diluted with 20 parts 1% $CaCl_2$. After a 3 minute immersion, the capsules are washed twice in 1% $CaCl_2$.

The capsules are then transferred to a 32 ml solution comprising 0.005% (w/v) polylysine (average MW 43,000 daltons) in physiological saline. After 3 minutes, the polylysine solution is decanted. The resulting capsules, having "permanent" semipermeable membranes, are then washed twice with 1% $CaCl_2$, twice with physiological saline, and mixed with 10 ml of 0.03 percent alginic acid solution.

The capsules resist clumping, and all can be seen to contain fibroblasts. Gel on the interior of the capsules is reliquified by immersing the capsules in a mixture of saline and citrate buffer (pH—7.4) for 5 minutes. All of the foregoing procedures are conducted at 22°-37° C.

Under the microscope, these capsules are observed to comprise a very thin membrane which enclose cells. Molecules having a molecular weight up to about one-hundred thousand can traverse the membranes.

The resulting capsules are suspended in CMLR-1969 supplemented with 10% fetal calf serum. After incubation at 37° C. for 4-5 days, the capsules, if examined under the microscope, will be found to contain fibroblasts which have undergone mitosis and display a classical fibroblastic morphology within the microcapsules.

The capsule membranes may be disrupted without damaging the cells by allowing a 10 ml portion of the microcapsule suspension containing about 500-1000 capsules per ml to settle. After aspiration of the medium, the capsules are washed twice with saline. The washed capsules are then mixed with a 3.0 ml aliquot containing 1000 units/ml heparin and 1.1% (w/v) $CaCl_2$. The suspension is agitated at 37° C. for 3 minutes, after which the capsules are allowed to settle, the supernatant is aspirated off, and the capsules are washed twice with 3.0 ml of 0.15M NaCl. After aspiration of the second wash solution, the capsules are mixed with 2.0 ml of a mixed solution comprising equal volumes of 110 mM sodium citrate and 0.15M NaCl (pH=7.4). The mixture is hand vortexed for 1 minute to induce dissolution of the membranes after which cells are washed twice in medium.

The fibroblasts are subjected to an IFN-$\beta$ superinduction technique according to the Vilcek procedure. Under a 5% $CO_2$ atmosphere (95% air), the cell suspension is incubated at 37° C. for one hour in the presence of 100 ug/ml Poly I-Poly C, a double stranded RNA (known IFN-$\beta$ inducer) available from PL Biochemicals, Milwaukee, Wis. and 50 ug/ml cycloheximide (protein synthesis inhibitor, Calbiochem, La Jolla, Calif.) After one hour, the suspended cells are washed in medium (CMLR-1969) containing 50 ug/ml cycloheximide and then resuspended in the same solution for 3 hours at 37° C. under a 5% $CO_2$ atmosphere. At the completion of this incubation the washing step is repeated and the cells are resuspended in medium containing 50 ug/ml cycloheximide and 5 ug/ml actimomycin D (a known RNA synthesis inhibitor, Calbiochem) and incubated for 2 hours at 37° C. under a 5% $CO_2$ atmosphere. The cells are then washed twice in medium and suspended in serum-free medium at 37° C. for 18-24 hours, during which time the fibroblasts secrete IFN-$\beta$, which has a molecular weight on the order of 21,000 daltons and may be harvested from the extracapsular medium.

In one experiment conducted with Poly I-Poly C(5S) (sedimentation value, Poly I and Poly C annealed to form double stranded RNA) 2,500 units of IFN-$\beta$ were produced per $10^5$ cells in the culture. An identical yield was obtained in a second run using Poly I-Poly C (12S) (double stranded as purchased).

Other embodiments are within the following claims.

What is claimed is:

1. A process for culturing anchorage dependent cells, said process comprising the steps of:
   A. suspending a cell in a medium containing an anchorage substrate material and high molecular weight components needed to maintain viability and to support mitosis of said cell;
   B. encapsulating said cell together with said medium and anchorage substrate material within a semipermeable membrane comprising a polysaccharide having plural anionic groups cross-linked with a polymer having plural cationic groups and a molecular weight greater than 3,000, said semipermeable membrane having an upper limit of permeability sufficient to preclude traverse of said anchorage substrate material and sufficient to allow low molecular weight molecules to traverse said membrane;
   C. suspending the product of step B in a culture medium sufficient to maintain viability and to support mitosis of said encapsulated cell; and
   D. allowing said cell to undergo mitosis within said membrane.

2. The process of claim 1 wherein said anchorage substrate is a protein.

3. The process of claim 1 wherein said anchorage substrate is collagen.

4. The process of claim 1 wherein the anchorage substrate is calf skin collagen and is included in said suspension at a concentration between about 10 ug/ml and 1.0 mg/ml.

5. The process of claim 1 comprising the additional step of selectively disrupting said membranes after step D to release said cells.

6. The process of claim 1 wherein said cell comprises a fibroblast.

7. The process of claim 1 wherein said high molecular weight components comprise serum components.

8. The process of claim 1 wherein said cell comprises a human fibroblast capable of secreting interferon.

9. The process of claim 1 wherein during said encapsulation step spheroidal membranes having an average diameter in the range of 100–500 microns are produced.

10. The process of claim 1 wherein said anchorage substrate comprises a protein having plural free cationic groups.

* * * * *

UNITED STATES PATENT AND TRADEMARK OFFICE
CERTIFICATE OF CORRECTION

PATENT NO. : 4,495,288

DATED : January 22, 1985

INVENTOR(S) : Franklin Lim

It is certified that error appears in the above-identified patent and that said Letters Patent are hereby corrected as shown below:

Page 1, after "Inventors:" delete --Allan P. Jarvis, Jr., Newburyport, Mass.;--

Column 4, line 33, after "1" insert --mg/ml--.

Column 9, line 21, delete "Humsn" and insert --Human--.

Signed and Sealed this

Twenty-seventh Day of August 1985

[SEAL]

Attest:

DONALD J. QUIGG

Attesting Officer

Acting Commissioner of Patents and Trademarks